United States Patent [19]

Chauvin et al.

[11] Patent Number: 4,795,734

[45] Date of Patent: Jan. 3, 1989

[54] RHENIUM-CONTAINING CATALYST FOR THE PRODUCTION OF OLEFINS BY METATHESIS

[75] Inventors: Yves Chauvin, Le Pecq; Dominique Commereuc, Meudon; Francois Hugues, Nanterre; Lucien Saussine, Croissy Sur Seine, all of France

[73] Assignee: Institut Francais Du Petrole, Rueil-Malmaison, France

[21] Appl. No.: 121,836

[22] Filed: Nov. 17, 1987

[30] Foreign Application Priority Data

Nov. 18, 1986 [FR] France ................................. 86 16129

[51] Int. Cl.$^4$ .......................... B01J 21/04; B01J 23/36
[52] U.S. Cl. ..................................... 502/355; 502/241; 502/300; 502/341; 502/351
[58] Field of Search ............... 502/300, 355, 241, 341, 502/351

[56] References Cited

U.S. PATENT DOCUMENTS 3,658,927  4/1972  Crain et al. ..................... 502/355 X

FOREIGN PATENT DOCUMENTS 0225953  6/1987  European Pat. Off. ............ 502/355
1054864  1/1967  United Kingdom ................ 502/300

*Primary Examiner*—W. J. Shine
*Attorney, Agent, or Firm*—Millen & White

[57] ABSTRACT

Process for manufacturing a rhenium-containing catalyst comprising three steps of:
  dry impregnation of an alumina-containing porous carrier, at a temperature lower than 80° C., for at least 10 hours,
  first thermal treatment at 85°–250° C., and
  second thermal treatment at 400°–1000° C.

The obtained catalyst can be used for producing olefins by metathesis of other olefins.

9 Claims, No Drawings

RHENIUM-CONTAINING CATALYST FOR THE PRODUCTION OF OLEFINS BY METATHESIS

The invention concerns a rhenium-containing catalyst, a process for manufacturing the same, and the use of said catalyst for producing olefins by metathesis.

BACKGROUND OF THE INVENTION

The metathesis reaction operates a redistribution of the alkylidene groups between olefins. It is particularly advantageous, for example, for restoring a balanced proportion between light olefins obtained by steam-cracking: ethylene, propylene and butenes.

Several types of catalysts are known as being capable to catalyze this reaction. They are either of the homogeneous type, when their constituting elements are all soluble in the reaction medium, or of the heterogeneous type, when at least one of the elements is insoluble in said medium. The latter are particularly advantageous when the active metal is costly and must accordingly be re-used without losses. Rhenium-containing catalysts are of this type. Their use in heterogeneous form has been recommended for catalyzing methathesis of simple olefins, for example in U.S. Pat. Nos. 3 641 189 and 3 676 520.

SUMMARY OF THE INVENTION

The invention concerns a process for obtaining catalysts of higher activity than those of the prior art.

This process comprises the steps of:
(a) impregnating an alumina-containing carrier with a rhenium compound solution,
(b) subsequently heating it to 85°–250° C., so as to remove at least a major part of the impregnation solvent, and
(c) performing a final heating at 400°–1000° C., so as to activate the catalyst.

The process is characterized in that the impregnation of the porous carrier is a dry impregnation, also called capillary impregnation, and in that the impregnated carrier, after addition of the rhenium compound solution, and before the heating step at 85°–250° C., is maintained for at least ten hours at a temperature of 0°–80° C. under substantially non-evaporating conditions, i.e. such that at least 85% and preferably at least 95% of the adsorbed solvent remains in the impregnated carrier.

By dry impregnation it is meant an impregnation with a volume of solution at most equal to the pore volume of the carrier; preferably the solution volume is at least 90% of the pore volume of the carrier.

The carrier consists preferably of alumina or of a mixture of at least 20% by weight of alumina with another refractory oxide, for example silica, magnesia or titanium oxide. This carrier must have a sufficiently high surface, for example at least 10 m$^2$/g, and a substantial pore volume, for example at least 0.1cc/g, preferably 0.3–1cc/g.

This minimum volume is a free liquid volume, since otherwise the impregnation could not be achieved. On the contrary, the nature of the gas filling the pores is unimportant. This gas may also have been expelled by vacuum operation.

Preferred rhenium compounds are rhenium heptoxide, ammonium perrhenate and perrhenic acid. The rhenium compound is dissolved in water or in an organic solvent, for example an alcohol such as methanol.

In addition to rhenium, other metals may be introduced into the catalyst.

Many examples are given in the technical literature and patents and it is thus unnecessary to give here an exhaustive list thereof.

The impregnated carrier is maintained at 0–80° C. for at least 10 hours, for example 10–1000 hours in the above-mentioned conditions. An impregnation period substantially longer than 10 hours will not result in additional advantages. On the contrary, a shorter period of impregnation and keeping at 0°–80° C., for example from 10 minutes to 2 hours, gives less active catalysts. This is a surprising fact inasmuch as it is generally considered that dry impregnation requires a much shorter impregnation period of about a few minutes, see for example: A. V. NEIMARK, L. I. KHEIFEZ, and V. B. FENELONOV in: Ind. Eng. Chem. Prod. Res. Dev., (1981) 20, 439–450, in particular page 441.

The object of the subsequent heating (step b) is to remove at least the major part of the solvent, preferably almost the entire amount thereof, and to stabilize rhenium. Heating for example at a temperature of 85°–250° C., preferably at 100°–180° C., during, for example, 30 minutes to 5 hours or more, gives satisfactory results. The operation may be conducted in a neutral atmosphere, for example by nitrogen scavenging, or in an oxidizing atmosphere, for example by air scavenging, or even under vacuum. Too short a heating period or too low a temperature must be avoided since it results in an incomplete stabilization and in a rhenium loss during the subsequent activation treatment. Conversely, too high a temperature leads to rhenium losses during the present step. The rhenium amount on the carrier is adjusted by selecting the concentration of the rhenium-containing impregnation solution. When the rhenium amount to be impregnated is higher than that which can be introduced by a solution at its saturation limit, the operation must be repeated several times, with, at each time, the succession of steps (a) and (b) up to the achievement of the desired rhenium content of the carrier. A solid is thus obtained which contains from 0.01 to 20% and preferably from 1 to 15% of rhenium, as dry weight.

The catalyst obtained after steps (a) and (b) is activated by heating between 400° and 1 000° C. (step c), preferably between 500° and 900° C. or between 60° and 1000° C., under an atmosphere of non reducing gas, e.g oxygen, nitrogen or argon, oxygen diluted with nitrogen, preferably as air, under static or dynamic conditions, a light gas flow being however preferable. In moistness content of the gas flow is preferably maintained lower than 200 ppm (parts per million). The heating step may also be conducted in atmosphere formed by the gases resulting from the combustion of methane in the presence of excess air. This activation treatment lasts for example from 10 minutes to 5 hours or more. After that, the obtained active catalyst is cooled, preferably under an anhydrous atmosphere. If necessary, a purge with nitrogen may be performed before contact with the hydrocarbon charge.

Olefins liable to undergo metathesis reaction catalyzed with the above-described rhenium supported catalyst include linear olefins complying with the general formula: $R_1R_2C=CR_3R_4$; wherein $R_1$, $R_2$, $R_3$ and $R_4$, identical or different, are hydrogen or a hydrocarbyl radical having 1 to 20 carbon atoms. The olefins may also have a ring structure, the ring containing 3–20 carbon atoms. The olefin may react with itself or with other olefins in an olefin mixture. An example of application concerns the production of propylene by reacting ethylene with 2-butenes, or the inverse reaction of converting propylene to an ethylene +2 butene mixture.

The methathesis reaction is preferably performed in the absence of solvent. However, the presence of such a solvent as an aliphatic, cyclanic or aromatic or a hydrocarbon halogenated hydrocarbon, is not detrimental.

The reaction may be performed in a stirred reactor, or by passing one or more reactants through a fixed, moving or fluidized catalyst bed.

The operation is mostly conducted at a temperature from 0° to 200° C., preferably from 20 to 120° C. The pressure is not critical.

The metathesis reaction is preferably performed in liquid phase, in the absence of oxygen and of moistness and the reactants and solvents are advantageously subjected to a prior treatment therefor.

EXAMPLES

The following examples are given to illustrate the invention and must not be considered as limiting the scope thereof.

EXAMPLE 1

Catalyst preparation 30 grams of a Y-alumina (specific surface: 187 m²/g, pore volume of 0.52 cc/g) are roasted in an air stream at 350° C. for 3 hours.

After cooling to room temperature, this alumina is impregnated with an aqueous solution of 1.66 g of ammonium perrhenate (corresponding to a 3.85% by weight theoretical rhenium content of the catalyst)in 15.6 cc of water, by dropwise introduction of the aqueous solution on the alumina and vigorous stirring. When the whole aqueous solution has been absorbed by alumina, i.e. after about five minutes, this solution is allowed to settle for 24 hours at 20° C. in a wet atmosphere. After that, the solid, whose weight is substantially unchanged, is brought, in 10 minutes, by means of an external oil bath, to a temperature of 140° C., under a pressure of 0.1 mmHg and maintained at these conditions for 2 hours. At this time, the catalyst is again placed in air at atmospheric pressure, then scavenged with an air stream containing 150 ppm of water, at a flow rate of 18 l/h. The temperature is progressively increased up to 800° C. and maintained at this level for 3 hours. The so-activated catalyst is cooled under an air stream to room temperature, then purged several times with nitrogen and stored under a nitrogen atmosphere.

Use for metathesis 17 grams of catalyst as above prepared are charged under moistness-proof conditions in a reactor consisting of a double-jacket tube with water circulation providing for the temperature regulation. Liquid propylene is injected through a pump onto the catalyst, from the reactor bottom, at a rate of 107 cc/h (volume flow rate/catalyst volume x hour: VVH=4.40). The temperature is 35° C. and the pressure in the reactor is maintained at 3.5 MPa by means of a regulator placed below the reactor. Under these conditions, 20% of the propylene at the reactor output are converted to an equimolar mixture of ethylene and 2-butenes. The selectivity is substantially 100%.

EXAMPLE 2

Catalyst preparation

A new catalyst batch is prepared as in example 1, except that, after impregnation with the aqueous solution of ammonium perrhenate, the impregnated catalyst is allowed to rest at room temperature in a wet atmosphere before being subjected to thermal treatment as described in example 1.

Use for metathesis 17 grams of the above-prepared catalyst are charged into the same apparatus as above described in example 1. Liquid propylene is introduced at a rate of 114.3 cc/h (VVH=4.70), at a temperature of 35° C. under a pressure of 3.5 MPa. The propylene conversion rate amounts to 18% (selectivity: substantially 100%).

EXAMPLE 3 (comparative)

This example forms no part of the invention, but is only given for purposes of comparison.

Catalyst preparation

A catalyst batch is prepared as in example 1, except that, after impregnation with the ammonium perrhenate aqueous solution, the impregnated catalyst is allowed to rest for only 15 minutes before being subjected to the thermal treatments described in example 1.

Use for metathesis 17 grams of the above-prepared catalyst are charged into the same apparatus as that described in example 1. Liquid propylene is introduced at a rate of 107 cc/h (VVH =4.40), at a temperature of 35° C. and under a pressure of 3.5 MPa. The propylene conversion is 10%. The selectivity is substantially 100%.

This example shows a lower activity of this catalyst batch.

EXAMPLE 4

Catalyst preparation 50 grams of Y-alumina used in example 1 are roasted in air stream at 350° C. for 3 hours. After cooling at 70° C., this alumina is impregnated with an aqueous solution of 5.53 g of ammonium perrhenate (catalyst theoretical rhenium content: 7.68% by weight)in 21 cc of water at 70° C. by dropwise introduction of the aqueous solution at 70° C. onto the alumina, with vigorous stirring. The alumina is then allowed to rest in a wet atmosphere for 20 hours at 70° C. After that, the solid is heated to a temperature of 140° C. under a pressure of 0.1 mmHg for 2 hours. At that time the catalyst is again subjected to air atmospheric pressure, then scavenged with an air stream containing 90 ppm of water, at a rate of 25 l/h. The temperature is progressively increased up to 550° C. and maintained at that level for 3 hours. The so-activated catalyst is cooled in an air stream at room temperature, the purged several time with nitrogen and stored under a nitrogen atmosphere.

Use for metathesis 17g of the above-prepared catalyst are charged into the apparatus described in example 1. Liquid propylene is injected at a rate of 71.4 cc/h (VVH =2.94), at a temperature of 70° C. and under a pressure of 5 MPa. The propylene conversion is 39% (selectivity: substantially 100%).

EXAMPLE 5

Catalyst preparation:

50g of Y-alumina used in example 1 are roasted under an air stream at 350° C. for 3 hours. After cooling at room temperature, this alumina is impregnated with an aqueous solution of perrhenic acid (21cc containing 3.85g of rhenium metal, i.e. a theoretical rhenium content of the catalyst equal to 7.7% by weight ), by dropwise introduction of the solution onto the alumina and vigorous stirring. The alumina is then allowed to rest in a wet atmosphere for 20 hours at 20° C. After this period, the solid, of substantially unchanged weight, is brought in 15 minutes to a temperature of 120° C. in a hot-air oven and maintained at these conditions for 2 hours. At this time, the catalyst is cooled and transferred to a furnace, where it is scavenged with a stream of gas formed by combustion of methane in the presence of excess air, thus progressively increasing the temperature up to 750° C., this temperature level being maintained for 30 minutes. This gas steam has the following composition in % by volume:

$CO_2$=4.58, $H_2O$=9.17, $O_2$=9.92, $N_2$=76.33

The so-activated catalyst is cooled in a stream of dry nitrogen to room temperature and then stored under a nitrogen atmosphere.

Use for metathesis 17g of the above-prepared catalyst are charged into the apparatus described in example 1. Liquid propylene is introduced at a rate of 107 cc/h (VVH =4.40), a temperature of 35° C. and under a pressure of 4.5 MPa. The propylene conversion is 35% ( selectivity: substantially 100% ).

What is claimed as the invention is:

1. A rhenium-containing catalyst obtained by dry-impregnating an alumina-containing porous carrier with a solution of a rhenium compound in a solvent, maintaining the impregnated carrier for at least 10 hours at a temperature of 0°-80° C. under substantially non-evaporating conditions after the end of the addition of the rhenium compound solution, heating the resultant material to 85°-250° C. for sufficient time to remove at least the major part of the impregnation solvent, and finally heating to 400°-1000° C. for activating the catalyst, said alumina containing carrier being alumina or a mixture of at least 20% by weight alumina with another refractory oxide, said carrier having a porosity of at least 0.1 cc/g and a surface of at least 10 m²/g.

2. A catalyst according to claim 1, characterized by a rhenium content of the impregnated catalyst from 0.01 to 20% by weight in proportion to the porous carrier.

3. A catalyst according to claim 1, wherein the rhenium compound pertains to the group consisting of rhenium heptoxide, ammonium perrhenate and perrhenic acid.

4. A catalyst according to claim 1, wherein the porous carrier is an alumina having a porosity of 0.3-1 cc/g.

5. A catalyst according to claim 1, wherein the heating at 85°-250° C. is conducted for 30 minutes to 5 hours in a neutral or oxidizing atmosphere or under vacuum, and followed with a heating at 400°-1000° C. for 10 minutes to 5 hours in a non-reducing atmosphere.

6. A catalyst according to claim 1, wherein the final heating step is conducted at 600°-1000° C. for 10 minutes to 5 hours in atmosphere of gas formed by methane combustion in the presence of an air excess air.

7. A catalyst according to claim 1 wherein the carrier is gamma alumina.

8. A catalyst according to claim 1 wherein the activating temperature is 500°-900° C.

9. A catalyst according to claim 1 wherein said alumina-containing carrier is said mixture and the refractory oxide is silica, magnesia or titanium oxide.

* * * * *